(12) United States Patent
Matsunaga et al.

(10) Patent No.: US 6,592,630 B2
(45) Date of Patent: Jul. 15, 2003

(54) HAIR DYE COMPOSITION

(75) Inventors: Kenichi Matsunaga, Sumida-ku (JP);
Hajime Miyabe, Sumida-ku (JP);
Yukihiro Ohashi, Sumida-ku (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 09/809,077

(22) Filed: Mar. 16, 2001

(65) Prior Publication Data

US 2001/0054206 A1 Dec. 27, 2001

(30) Foreign Application Priority Data

Mar. 17, 2000 (JP) .................................... 2000-076667

(51) Int. Cl.[7] ................................................ A61K 7/13
(52) U.S. Cl. ..................... 8/405; 8/406; 8/407; 8/409; 8/426; 8/437; 8/454
(58) Field of Search .......................... 8/405, 406, 407, 8/409, 426, 437, 454

(56) References Cited

U.S. PATENT DOCUMENTS

| | | | | |
|---|---|---|---|---|
| 5,520,707 A | | 5/1996 | Lim et al. ....................... | 8/426 |
| 5,593,459 A | * | 1/1997 | Gamblin ......................... | 8/539 |
| 5,733,343 A | | 3/1998 | Moeckli .......................... | 8/426 |
| 5,879,412 A | | 3/1999 | Rondeau et al. ............... | 8/411 |
| 5,888,252 A | | 3/1999 | Moeckli .......................... | 8/426 |
| 5,980,587 A | | 11/1999 | Samain ........................... | 8/426 |
| 5,993,490 A | * | 11/1999 | Rondeau et al. ............... | 8/409 |

FOREIGN PATENT DOCUMENTS

| | | |
|---|---|---|
| JP | 53-8619 | 1/1978 |
| JP | 58-2204 | 1/1983 |
| JP | 6-271435 | 9/1994 |
| JP | 8-501322 | 2/1996 |
| JP | 8-507545 | 8/1996 |
| JP | 9-118832 | 5/1997 |
| JP | 10-502946 | 3/1998 |
| JP | 10-194942 | 7/1998 |

* cited by examiner

*Primary Examiner*—Margaret Einsmann
*Assistant Examiner*—Eisa Elhilo
(74) *Attorney, Agent, or Firm*—Oblon, Spivak, McClelland, Maier & Neustadt, P.C.

(57) ABSTRACT

Provided is a hair dye composition containing a direct dye (1) or (2). The hair dye composition has markedly high hair dyeing power, has less color fade over time and undergoes a smaller change in the color tone of the dye after storage.

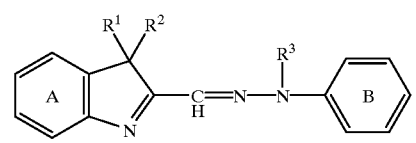

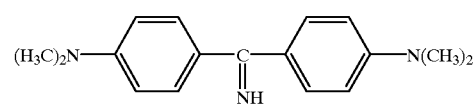

[$R^1$, $R^2$ and $R^3$ are the same or different and each independently represents a $C_{1-3}$ alkyl group and benzene ring A or B may contain a nondissociative substituent].

8 Claims, No Drawings

HAIR DYE COMPOSITION

TECHNICAL FIELD

The present invention relates to a hair dye composition which has markedly high hair dyeing power, can impart the hair with a vivid and deep color shade ranging from greenish yellow to reddish yellow, has less color fade over time and undergoes a smaller change in the color tone of the dye even after storage.

BACKGROUND ART

Hair dyes can be classified by the dye to be used therefor, or whether they have bleaching action of melanin or not. Typical examples include a two-part permanent hair dye composed of a first part containing an alkali agent, an oxidation dye and a direct dye such as nitro dye and a second part containing an oxidizing agent; and one-part semi-permanent hair dye containing an organic acid or an alkali agent, and a direct dye such as acid dye, basic dye or nitro dye.

The above-described permanent hair dye is however accompanied with the drawbacks that color tone imparted by an oxidation dye is not so vivid and the color of the hair dyed with a vivid-color producing nitro dye ordinarily employed as a direct dye markedly fades over time and becomes dull soon even if the color tone rightly after dyeing is very vivid (Japanese Patent Application Laid-Open (Kokai) No. Hei 6-271435).

Recently, hair dyes containing as a direct dye a so-called cationic dye having a cation group contained in their conjugate system have been reported (Japanese Language Laid-Open Publication (PCT) No. Hei 8-507545, 8-501322 or 10-502946, or Japanese Patent Application Laid-Open (Kokai) No. Hei 10-194942). They have been found to involve drawbacks that intended dyeing effects are not available owing to decomposition of them caused by mixing, upon hair dyeing, with hydrogen peroxide ordinarily employed as an oxidizing agent; and that when the cation group is incorporated in an azo(—N═N)-based conjugated system, they are unstable to an alkali agent or a reducing agent essentially contained in a permanent hair dye.

DISCLOSURE OF THE INVENTION

An object of the present invention is to provide a hair dye composition which features high hair dyeing power, less color fade over time and excellent storage stability permitting only a smaller color tone change of the dye after storage.

The present inventors have found that when the below-described compound which is known (in Japanese Patent Application Laid-Open (Kokai) No. Sho 53-8619) as a disperse dye for dry transfer printing of acidic modified synthetic fibers or as C.I. Basic Yellow 2 is used as a hair dye, the resulting dye composition can impart the hair with a vivid and deep color shade ranging from greenish yellow to reddish yellow without decomposing the dye upon hair dyeing, exhibits excellent light resistance, washing resistance, perspiration resistance, friction resistance and weather resistance, and undergoes a smaller change in the color tone of the dye after storage as compared with that rightly after preparation, because it exists stably in the composition.

In one aspect of the present invention, there is thus provided a hair dye composition comprising, as a direct dye, an azamethine compound represented by the following formula (1):

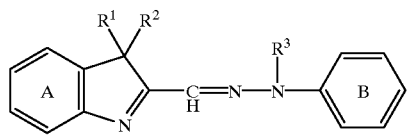

(1)

[wherein, $R^1$, $R^2$ and $R^3$ are the same or different and each independently represents a $C_{1-3}$ alkyl group and benzene ring A or B may contain a nondissociative substituent; or the following formula (2):

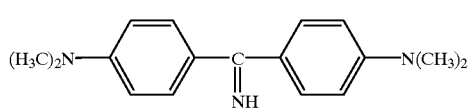

(2)

In another aspect of the present invention, there is also provided a method for dyeing the hair with the above-described hair dye composition.

BEST MODE FOR CARRYING OUT THE INVENTION

Compound (1) is known in Japanese Patent Application Laid-Open (Kokai) No. Sho 53-8619 as a diperse dye for dry transfer printing of acidic modified fibers, while Compound (2) is known as C.I. Basic Yellow 2. By the use of this Compound (1) or (2) as a direct dye for a hair dye composition, the hair can be imparted with a vivid and deep color shade ranging from greenish yellow to reddish yellow.

In the formula (1), examples of the $C_{1-3}$ alkyl group represented by $R^1$, $R^2$ or $R^3$ include methyl, ethyl and propyl groups.

In the formula (1), examples of the nondissociative substituent which may be possessed by benzene ring A or B include methyl group, ethyl group, propyl group, methoxy group, ethoxy group, chlorine atom and nitro group.

Specific examples of the direct dye (1) to be used in the present invention include the following compounds:

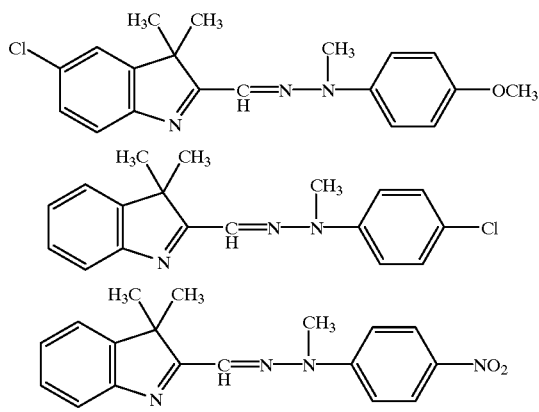

-continued

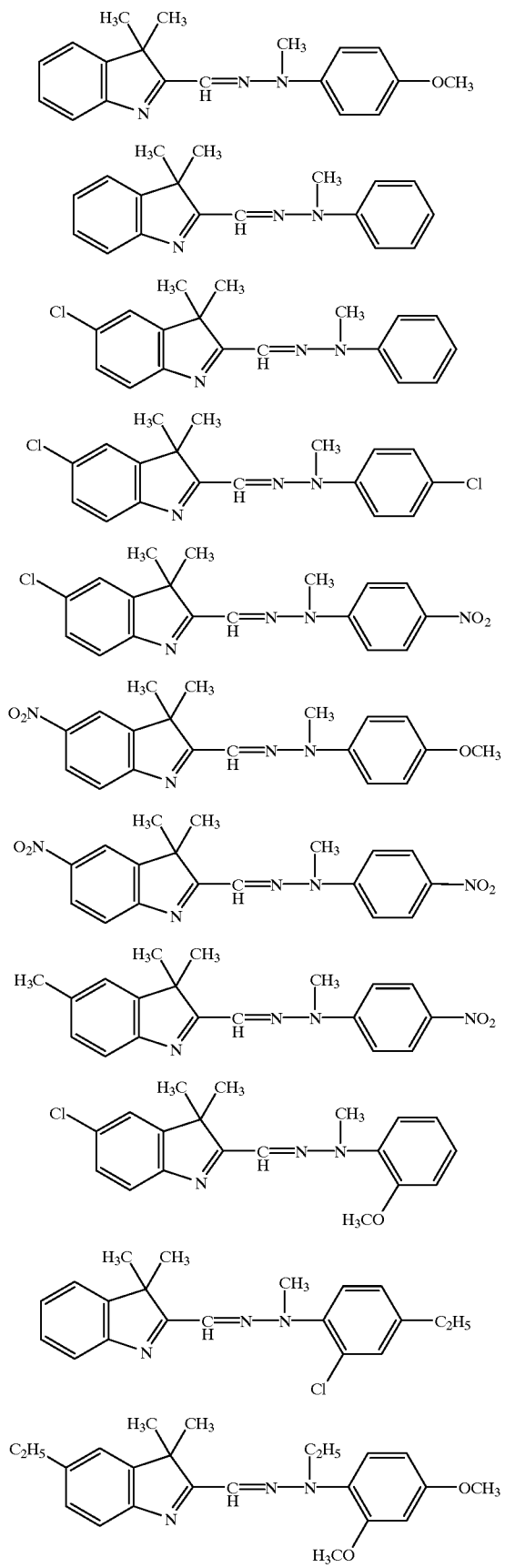
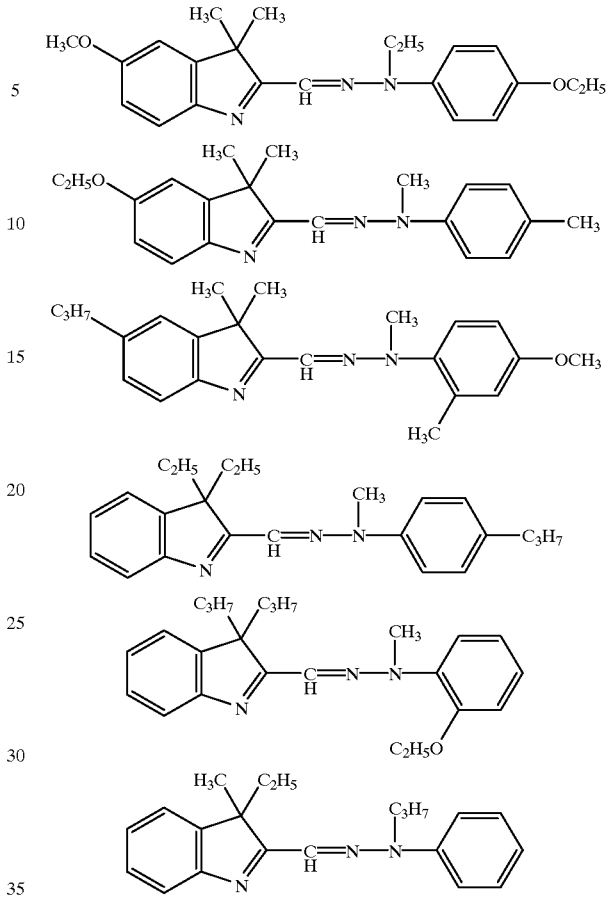

As the direct dye (1) or (2), one or more of them may be used. Alternatively, another direct dye can be used in combination. In particular, combination with a red or blue dye makes it possible to dye the hair with a deep and highly lustrous dark brown or black color.

Examples of the direct dye other than the direct dyes (1) and (2) include Basic Blue 7 (C.I. 42595), Basic Blue 26 (C.I. 44045), Basic Blue 99 (C.I. 56059), Basic Violet 10 (C.I. 45170), Basic Violet 14 (C.I. 42515), Basic Brown 16 (C.I. 12250), Basic Brown 17 (C.I. 12251), Basic Red 2 (C.I. 50240), Basic Red 22 (C.I. 11055), Basic Red 76 (C.I. 12245), Basic Red 118 (C.I. 12251:1) and Basic Yellow 57(C.I. 12719); and basic dyes as described in Japanese Patent Publication No. Sho 58-2204, Japanese Patent Application Laid-Open No. Hei 9-118832, Japanese Language Laid-Open Publication (PCT) No. Hei 8-501322 or Japanese Language Laid-Open Publication (PCT) No. Hei 8-507545.

The direct dye (1) or (2) is preferably added in an amount of 0.01 to 20 wt. %, more preferably 0.05 to 10 wt. %, especially 0.1 to 5 wt. % on the basis of the entirety of the composition (after mixing of all the parts when a two-part or three-part composition is employed; this will apply equally hereinafter). When another direct dye is used in combination, the content of it with the direct dye (1) or (2) preferably ranges from 0.05 to 10 wt. %, especially 0.1 to 5 wt. % based on the whole composition.

The hair dye composition of the present invention is preferably adjusted to pH 6 to 11, with pH 8 to 11 being more preferred. Examples of the alkali agent to be used for pH adjustment includes ordinarily employed ones such as ammonia, organic amines and salts thereof. The alkali agent is preferably added in an amount of 0.01 to 20 wt. %, more preferably 0.1 to 10 wt. %, especially 0.5 to 5 wt. %.

In the hair dye composition of the present invention, an oxidizing agent can be incorporated. In this case, hair dyeing and bleaching can be carried out simultaneously, which facilitates more vivid hair dyeing. Ordinarily employed oxidizing agents, for example, hydrogen peroxide, persulfates such as ammonium persulfate, potassium persulfate and sodium persulfate, perborates such as sodium perborate, percarbonates such as sodium percarbonate and bromates such as sodium bromate and potassium bromate are usable. Out of them, hydrogen peroxide is especially preferred. The oxidizing agent is added in an amount of 0.5 to 10 wt. %, especially 1 to 8 wt. %, on the basis of the entirety of the composition.

In the hair dye composition of the present invention, an oxidation dye can be incorporated further. This incorporation enables markedly vivid dyeing not attainable by the single use of an oxidation dye. As the oxidizing agent, the above-exemplified oxidizing agents can be used, with hydrogen peroxide being particularly preferred. Alternatively, an oxidizing enzyme such as laccase can be employed. For the oxidation dye, known developers and couplers ordinarily employed for an oxidation type hair dye can be used.

Examples of the developer include p-phenylenediamines having one or several groups selected from $NH_2$—, NHR— and $NR_2$-groups (R represents a $C_{1-4}$ alkyl or hydroxyalkyl group) such as p-phenylenediamine, p-toluylenediamine, N-methyl-p-phenylenediamine, chloro-p-phenylenediamine, 2-(2'-hydroxyethylamino)-5-aminotoluene, N,N-bis-(2-hydroxyethyl)-p-phenylenediamine, 2-hydroxyethyl-p-phenylenediamine, 2,6-dimethyl-p-phenylenediamine, methoxy-p-phenylenediamine, 2,6-dichloro-p-phenylenediamine, 2-chloro-6-methyl-p-phenylenediamine, 6-methoxy-3-methyl-p-phenylenediamine, 2,5-diaminoanisole, N-(2-hydroxypropyl)-p-phenylenediamine and N-2-methoxyethyl-p-phenylenediamine; 2,5-diaminopyridine derivatives and 4,5-diaminopyrazole derivatives; p-aminophenols such as p-aminophenol, 2-methyl-4-aminophenol, N-methyl-p-aminophenol, 3-methyl-4-aminophenol, 2,6-dimethyl-4-aminophenol, 3,5-dimethyl-4-aminophenol, 2,3-dimethyl-4-aminophenol and 2,5-dimethyl-4-aminophenol; o-aminophenols, o-phenylenediamines, 4,4'-diaminophenylamine and hydroxypropylbis(N-hydroxyethyl-p-phenylenediamine); and salts thereof.

Examples of the coupler include 1-naphthol, 1,5-dihydroxynaphthalene, 1,7-dihydroxynaphthalene, 2,7-dihydroxynaphthalene, 5-amino-2-methylphenol, 5-(2'-hydroxyethylamino)-2-methylphenol, 2,4-diaminoanisole, m-toluylenediamine, resorcin, m-phenylenediamine, m-aminophenol, 4-chlororesorcin, 2-methylresorcin, 2,4-diaminophenoxyethanol, 2,6-diaminopyridine, 2-amino-3-hydroxypyridine, 4-hydroxyindole, 6-hydroxyindole, 2,4-diamino-6-hydroxypyrimidine, 2,4,6-triaminopyrimidine, 2-amino-4,6-dihydroxypyrimidine, 4-amino-2,6-dihydroxypyrimidine, 4,6-diamino-2-hydroxypyrimidine and 1,3-bis(2,4-diaminophenoxy)propane; and salts thereof.

As a developer or coupler, at least one of the above-exemplified ones can be used. Although no particular limitation is imposed on its content, it is added in an amount of 0.01 to 20 wt. %, especially 0.5 to 10 wt. % based on the whole composition.

To the hair dye composition of the present invention, a known autoxidation dye typified by an indole or an indoline, or a known direct dye such as a nitro dye or a disperse dye can also be added.

Addition of a polyol, polyol alkyl ether, cationic or amphoteric polymer or silicone to the hair dye composition of the present invention is preferred, because the resulting hair dye composition can dye the hair uniformly and has improved cosmetic effects.

In addition to the above-described components, those ordinarily employed as a raw material for cosmetics can be added to the hair dye composition of the present invention, within an extent not impairing the advantages of the present invention. Examples of such an optional component include hydrocarbons, animal or vegetable fats and oils, higher fatty acids, organic solvents, penetration promoters, cationic surfactants, natural or synthetic polymers, higher alcohols, ethers, amphoteric surfactants, nonionic surfactants, protein derivatives, amino acids, antiseptics, chelating agents, stabilizing agents, antioxidants, plant extracts, crude drug extracts, vitamins, colorants, perfumes and ultraviolet absorbers.

The hair dye composition of the present invention can be prepared in a conventional manner into a one-part composition, a two-part composition having a first-part component containing an alkali agent and a second-part component containing an oxidizing agent, or a third-part composition having, in addition to these two components, a powdery oxidizing agent such as persulfate. The direct dye (1) or (2) can be incorporated in either one or both of these components of the two-part or three-part composition. The one-part type is applied to the hair directly, while the two- or three-part type is applied to the hair after mixing these parts upon hair dyeing.

No particular limitation is imposed on the form of the hair dye composition of the present invention. Examples include powder, transparent liquid, emulsion, cream, gel, paste, aerosol, and aerosol foam. It preferably has a viscosity of 2000 to 100000 mPa·s in the stage of application to the hair (after mixing of all the parts when a two-part or three-part type composition is employed).

EXAMPLES

Compounds employed in the below-described examples are as follows:

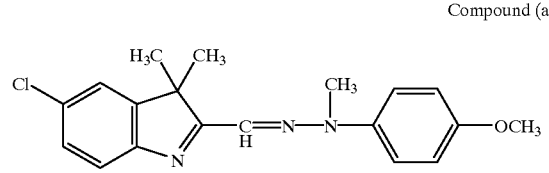

Compound (a)

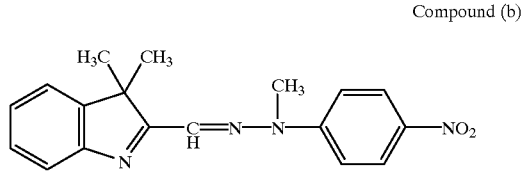

Compound (b)

Compound (c)

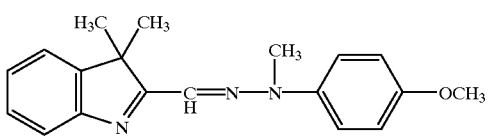

Compound (d)

(Basic Yellow 2)

Compound (e)

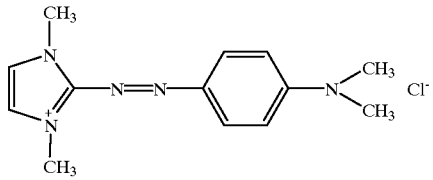

EXAMPLES 1 TO 5

In a manner known per se in the art, hair dyes as shown in Table 1 were prepared. The data appearing in Table 1 is represented by wt. %.

TABLE 1

| | Examples | | | | |
|---|---|---|---|---|---|
| | 1 | 2 | 3 | 4 | 5 |
| Dye [Compound (a)] | 0.2 | | 0.15 | 0.1 | |
| Dye [Compound (d)] | | 0.5 | | 0.1 | 0.2 |
| Dye [Compound (e)] | | | 0.15 | 0.1 | 0.05 |
| Dye [Basic Blue 26] | | | | 0.1 | 0.1 |
| Ethanol | | 5 | | 5 | 5 |
| Propylene glycol | | | 5 | | 5 |
| Diethylene glycol monoethyl ether | | 10 | | | |
| Guar gum | 1 | | | | |
| Hydroxypropyl guar gum | | 1 | 1 | 1 | 1 |
| "Gufguat 734" (trade name; product of ISP Japan) | 1 | 1 | | | |
| "Catinal LC100" (trade name; product of Toho Chemical Industry) | | 1 | | | 1 |
| "Polyether-modified silicone KF6005" (trade name; product of Shin-Etsu Chemical) | | | | 0.4 | |
| "Amodimethicone SM8702C" (trade name; product of Dow Corning Toray Silicone) | | | | 1.5 | |
| Monoethanolamine | | | 0.1 | | |
| Phosphoric acid | | Amount to adjust pH to 9 | | | |
| Perfume | | q.s. | | | |
| Water | | Balance | | | |
| Total (g) | | 100 | | | |

EXAMPLES 6 TO 9

In a manner known per se in the art, hair dyes as shown in Table 2 were prepared. The data appearing in Table 2 is represented by wt. %.

TABLE 2

| | Examples | | | |
|---|---|---|---|---|
| | 6 | 7 | 8 | 9 |
| 1st part | | | | |
| Dye [Compound (b)] | 0.2 | | 0.15 | 0.2 |
| Dye [Compound (d)] | | 0.1 | 0.15 | |
| Dye [Compound (e)] | | 0.2 | | 0.05 |
| Dye [Basic Blue 99] | | 0.3 | | |
| 28 wt. % aqueous ammonia | | 5 | | |
| Monoethanolamine | | 2 | | |
| Propylene glycol | | 8 | | |
| Polyoxyethylene (20) isostearyl ether | | 24 | | |
| Polyoxyethylene (2) isostearyl ether | | 20 | | |
| "Merquat 280" (trade name; product of Calgon Corp., a 35 wt. % aqueous solution) | 8 | | | |
| "Polymer JR400" (trade name; product of Union Carbide) | | 0.5 | | 0.5 |
| "Amodimethicone SM8702C" (trade name; product of Dow Corning Toray Silicone) | | | 2 | |
| "Polyether modified silicone KF6005" (trade name; product of Shin-Etsu Chemical) | | | | 0.3 |
| Tetrasodium ethylenediaminetetraacetate | | 0.1 | | |
| Perfume | | q.s. | | |
| Ammonium chloride | | Amount to adjust pH to 10 | | |
| Water | | Balance | | |
| 2nd part | | | | |
| 35 wt. % aqueous hydrogen peroxide | | 17.1 | | |
| Methylparaben | | 0.1 | | |
| Phosphoric acid | | Amount to adjust pH to 3.5 | | |
| Water | | Balance | | |

EXAMPLES 10 TO 12

In a manner known per se in the art, hair dyes as shown in Table 3 were prepared. The data appearing in Table 3 is represented by wt. %.

TABLE 3

| | Examples | | |
|---|---|---|---|
| | 10 | 11 | 12 |
| 1st part | | | |
| Toluene-2,5-diamine | 1.9 | 1 | |
| Para-aminophenol | | | 1 |
| Resorcin | 2 | | |
| Para-amino-ortho-cresol | | | 1.1 |
| 2,4-Diaminophenoxyethanol | | 1.37 | |
| Dye [Compound (b)] | 0.05 | | |
| Dye [Compound (d)] | | 0.15 | |
| Dye [Compound (c)] | | | 0.1 |
| 28 wt. % aqueous ammonia | | 5 | |
| Monoethanolamine | | 2 | |
| Propylene glycol | | 8 | |
| Polyoxyethylene (20) isostearyl ether | | 24 | |
| Polyoxyethylene (2) isostearyl ether | | 20 | |
| "Merquat 280" (trade name; product of Calgon Corp., a 35 wt. % aqueous solution) | 8 | | |
| "Polymer JR400" (product of Union Carbide) | | 0.5 | |
| "Amodimethicone SM8702C" (trade name; product of Dow Corning Toray Silicone) | | | 2 |
| Sodium sulfite | | 0.05 | |
| Ascorbic acid | | 0.5 | |
| Tetrasodium ethylenediaminetetraacetate | | 0.1 | |
| Perfume | | q.s. | |
| Ammonium chloride | | Amount to adjust pH to 10 | |
| Water | | Balance | |

TABLE 3-continued

|  | Examples | | |
|---|---|---|---|
|  | 10 | 11 | 12 |
| 2nd part | | | |
| 35 wt. % Aqueous hydrogen peroxide | | 17.1 | |
| Methylparaben | | 0.1 | |
| Phosphoric acid | Amount to adjust pH to 3.5 | | |
| Water | | Balance | |

EXAMPLE 13

In a manner known per se in the art, the following hair dye was prepared.

| | (wt. %) |
|---|---|
| (First part) | |
| Para-aminophenol | 1 |
| Para-amino-ortho-cresol | 1.1 |
| Compound (d) | 0.1 |
| 28 wt. % aqueous ammonia | 5 |
| Monoethanolamine | 2 |
| Cetanol | 8.5 |
| Polyoxyethylene (40) cetyl ether | 3 |
| Polyoxyethylene (2) cetyl ether | 3.5 |
| Stearyl trimethyl ammonium chloride | 2 |
| Liquid paraffin | 0.5 |
| Sodium sulfite | 0.05 |
| Ascorbic acid | 0.5 |
| Tetrasodium ethylenediaminetetraacetate | 0.1 |
| Perfume | q.s. |
| Ammonium chloride | Amount to adjust pH to 10 |
| Water | Balance |
| (Second part) | |
| 35 wt. % Aqueous hydrogen peroxide | 17.1 |
| Methyl paraben | 0.1 |
| Phosphoric acid | Amount to adjust pH to 3.5 |
| Water | Balance |

What is claimed is:

1. A hair dye composition, comprising:

an oxidizing agent and/or an oxidation dye, and, as a direct dye, an azamethine compound represented by the following formula (1):

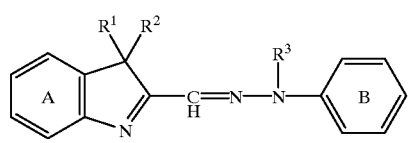

(1)

wherein, $R^1$, $R^2$ and $R^3$ are the same or different and each independently represents a $C_{1-3}$ alkyl group and benzene ring A or B may have a nondissociative group; wherein said hair dye composition has a pH of from 8 to 11.

2. The hair dye composition of claim 1, wherein said azamethine compound of formula (1) is selected from the group consisting of

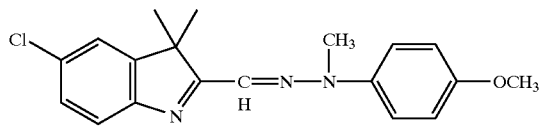
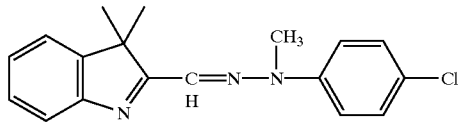
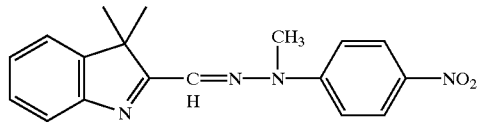
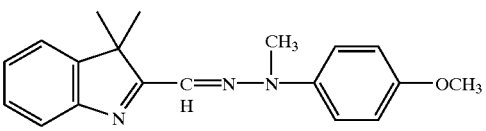
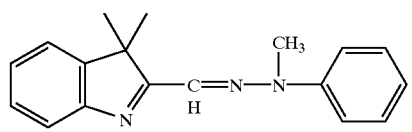
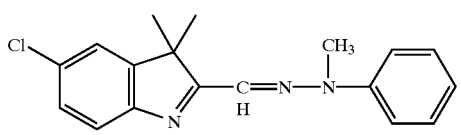
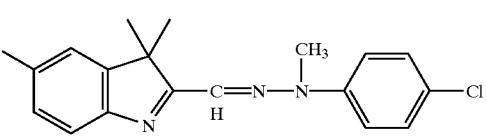
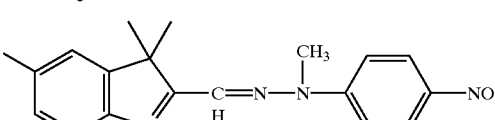
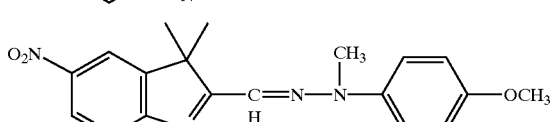
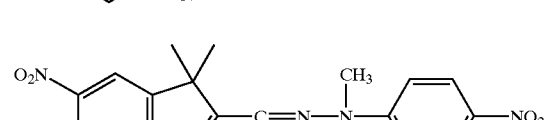
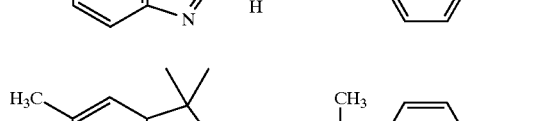
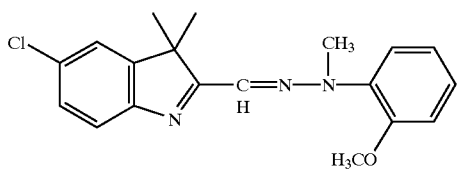

-continued

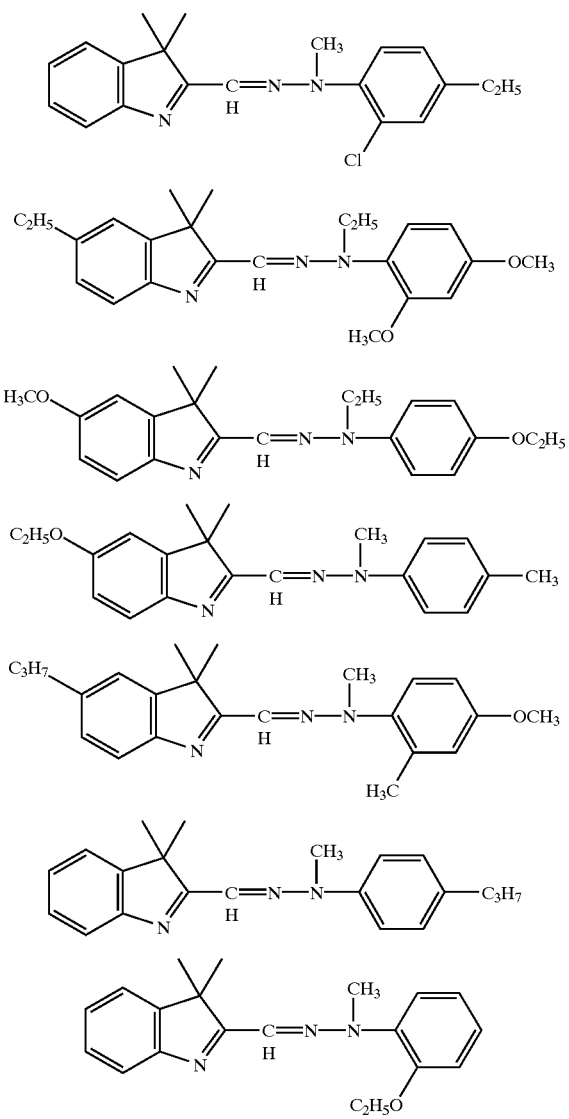

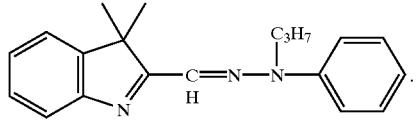

3. The hair dye composition of claim 1, wherein said direct dye is present in the amount of 0.01–20% by weight.

4. The hair dye composition of claim 1, wherein said oxidizing agent is present in an amount of 0.5–10% by weight.

5. The hair dye composition of claim 1, wherein said nondissociative substituent is selected from the group consisting of a methyl group, an ethyl group, a propyl group, a methoxy group, an ethoxy group, a chlorine atom and a nitro group.

6. A method for dyeing the hair with a dye composition, comprising:

applying said dye composition comprising, as a direct dye, an azamethine compound represented by the following formula (1)

(1)

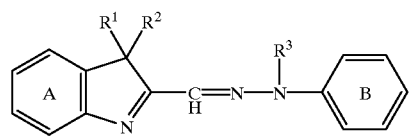

wherein, $R^1$, $R^2$ and $R^3$ are the same of different and each independently represents a alkyl group and benzene ring A or B may have a nondissociative group, to the hair, wherein said dye composition has a pH of from 8 to 11.

7. The method of claim 6, wherein said hair dye composition further comprises an oxidizing agent.

8. The method of claims 6 or 7, wherein, said hair dye composition further comprises an oxidation dye.

* * * * *

UNITED STATES PATENT AND TRADEMARK OFFICE
CERTIFICATE OF CORRECTION

PATENT NO.    : 6,592,630 B2
DATED         : July 15, 2003
INVENTOR(S)   : Kenichi Matsunaga et al.

It is certified that error appears in the above-identified patent and that said Letters Patent is hereby corrected as shown below:

Column 11,
Line 35,

Line 40, 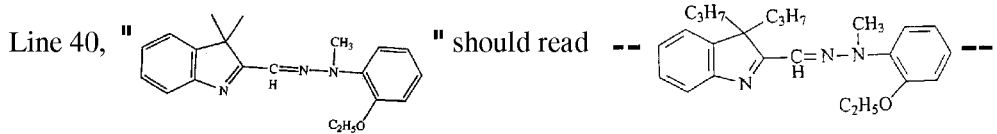

Column 12,
Line 5, 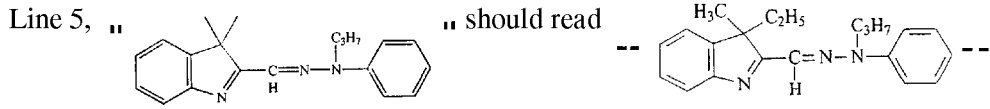

Line 35, "represents a alkyl" should read -- represents a $C_{1-3}$ alkyl --.

Signed and Sealed this

Twenty-fifth Day of November, 2003

JAMES E. ROGAN
*Director of the United States Patent and Trademark Office*